US011930832B2

United States Patent
Martin et al.

(10) Patent No.: US 11,930,832 B2
(45) Date of Patent: *Mar. 19, 2024

(54) FEED SUPPLEMENT MATERIAL FOR USE IN AQUACULTURE FEED

(71) Applicant: DSM IP ASSETS B.V., Heerlen (NL)

(72) Inventors: Christian Martin, Kaiseraugst (CH); Ester Santigosa, Kaiseraugst (CH); Vivien Verlhac, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 48 days.

This patent is subject to a terminal disclaimer.

(21) Appl. No.: 17/111,459

(22) Filed: Dec. 3, 2020

(65) Prior Publication Data
US 2021/0127715 A1 May 6, 2021

Related U.S. Application Data

(63) Continuation of application No. 15/533,775, filed as application No. PCT/EP2015/079417 on Dec. 11, 2015, now Pat. No. 10,874,120.

(30) Foreign Application Priority Data

Dec. 12, 2014 (EP) .................................... 14197713
Dec. 18, 2014 (EP) .................................... 14020113

(51) Int. Cl.
*A23K 50/80* (2016.01)
*A01K 61/13* (2017.01)
(Continued)

(52) U.S. Cl.
CPC .............. *A23K 50/80* (2016.05); *A01K 61/13* (2017.01); *A23K 10/16* (2016.05); *A23K 20/10* (2016.05); *A23K 20/158* (2016.05); *C12P 7/6427* (2013.01)

(58) Field of Classification Search
CPC ........ A23K 50/80; A23K 20/158; A23K 20/10; A23K 10/16; A23K 10/18; A01K 61/13; C12P 7/6472
See application file for complete search history.

(56) References Cited

U.S. PATENT DOCUMENTS 7,932,077 B2   4/2011   Damude
9,668,499 B2   6/2017   Apt et al.
(Continued)

FOREIGN PATENT DOCUMENTS

CL   200700006   6/2007
CN   102884201   1/2013
(Continued)

OTHER PUBLICATIONS

Ganuza et al., "Crypthecodinium cohnii and *Schizochytrium* sp. as potential substitutes to fisheries-delivered oils from seabream (*Sparus aurata*) microdiets", Aquaculture, vol. 277, No. 1-2, pp. 109-116.
(Continued)

*Primary Examiner* — Trinh T Nguyen
(74) *Attorney, Agent, or Firm* — NIXON & VANDERHYE P.C.

(57) ABSTRACT

The invention concerns a method of sustainably producing an aquaculture meat product by feeding a fish over its dietary cycles an aquaculture feed composition, said method comprising the step of formulating an aquaculture feed composition by replacing all or part of fish oil in the composition with a single microbial source of eicosapentaenoic acid ("EPA") and docosahex-aenoic acid ("DHA"). In a preferred embodiment, the microbial source comprising DHA and EPA derives from a microorganism/microbe of the genus *Schizochytrium* or *Thraustochytrium*.

17 Claims, 2 Drawing Sheets (51) Int. Cl.
*A23K 10/16* (2016.01)
*A23K 20/10* (2016.01)
*A23K 20/158* (2016.01)
*C12P 7/6427* (2022.01)

(56) References Cited

U.S. PATENT DOCUMENTS

| | | | |
|---|---|---|---|
| 2007/0082008 | A1 | 4/2007 | Harel et al. |
| 2007/0226814 | A1 | 9/2007 | Kiy |
| 2010/0285105 | A1 | 11/2010 | Radianimgtyas |
| 2011/0177031 | A1 | 7/2011 | Apt et al. |
| 2012/0204802 | A1 | 8/2012 | Nichols et al. |
| 2021/0289817 | A1* | 9/2021 | Arriagada ............... A23K 50/80 |
| 2021/0310032 | A1* | 10/2021 | Lowrey ................. C12P 7/6434 |

FOREIGN PATENT DOCUMENTS

| | | |
|---|---|---|
| JP | 2013-516997 | 5/2013 |
| WO | 2005/027651 | 3/2005 |
| WO | WO 2012/021703 | 2/2012 |
| WO | 2013/010090 | 1/2013 |

OTHER PUBLICATIONS

International Search Report for PCT/EP2015/079417 dated Mar. 9, 2016, 4 pages.
Written Opinion of the ISA for PCT/EP2015/079417 dated Mar. 9, 2016, 5 pages.
Examination Report No. 1 for Standard Patent Application, AU Patent Appln. No. 2015359335, dated Jan. 11, 2019.
Communication Pursuant to Article 94(3) EPC, EP Appln. No. 15817121.5-1105, dated May 29, 2019.
Engström et al, "*Effect of fish oils containing different amounts of EPA, DHA, and antioxidants on plasma and brain fatty acids and brain nitric oxide synthase activity in rats*", Upsala Journal of Medical Sciences, vol. 114, No. 4, Dec. 1, 2009, pp. 206-213.
Anon, "*Oil rich in docosahexaenoic acid (DHA) and eicosapentaenoic acid (EPA)*", XP55591451, Jan. 1, 2012.
Notice of Reasons for Rejection, JP Appln No. P2017-527283, dated Jun. 4, 2019.
Final Rejection, JP Patent Appln. No. P2017-527283, dated Nov. 12, 2019.

* cited by examiner

FEED SUPPLEMENT MATERIAL FOR USE IN AQUACULTURE FEED

CROSS-REFERENCE

This application is a continuation of commonly owned U.S. application Ser. No. 15/533,775 (now U.S. Pat. No. 10,874,120), filed Jun. 7, 2017 which is the U.S. national phase of International Application No. PCT/EP2015/079417 filed Dec. 11, 2015 which designated the U.S. and claims priority to EP Patent Application No. 14197713.2 filed Dec. 12, 2014 and EP Patent Application No. 14020113.8 filed Dec. 18, 2014, the entire contents of each of which are hereby incorporated by reference.

This invention is in the field of aquaculture. More specifically, this invention pertains to a method of sustainably producing an aquaculture meat product by feeding a fish over its dietary cycles an aquaculture feed composition that includes at least a reduced a reduced amount of fish oil.

Aquaculture is a form of agriculture that involves the propagation, cultivation and marketing of aquatic animals and plants in a controlled environment. The aquaculture industry is currently the fastest growing food production sector in the world. World aquaculture produces approximately 60 million tons of seafood, which is worth more than $70 billion (US) annually. Today, farmed fish accounts for approximately 50% of all fish consumed globally. This percentage is expected to increase as a result of dwindling catches from capture fisheries in both marine and freshwater environments and increasing seafood consumption (i.e., total and per capita). Today, species groups in aquaculture production include, for example: carps and other cyprinids; 15 oysters; clams, cockles and arkshells; shrimps and prawns; salmons, trouts and smelts; mussels; tilapias and other cichlids; and scallops.

While some aquacultured species (e.g., *Tilapia*) can be fed on an entirely vegetarian diet, many others species are fed a carnivorous diet. Typically, the feed for carnivorous fish comprises fishmeal and fish oil derived from wild caught species of 20 small pelagic fish (predominantly anchovy, jack mackerel, blue whiting, capelin, sandeel and menhaden). These pelagic fish are processed into fishmeal and fish oil, with the final product often being either a pelleted or flaked feed, depending on the size of the fish. The other components of the aquaculture feed composition may include vegetable protein, vitamins, minerals and pigment as required.

Marine fish oils have traditionally been used as the sole dietary lipid source in commercial fish feed given their ready availability, competitive price and the abundance of essential fatty acids contained within this product. Additionally, fish oils readily supply essential fatty acids which are required for regular growth, health, reproduction and bodily functions within fish. More specifically, all vertebrate species, 30 including fish, have a dietary requirement for both omega-6 and omega-3 polyunsaturated fatty acids ["PUFAs"]. Eicosapentaenoic acid ["EPA"; cis-5, 8,11,14,17-eicosapentaenoic acid; omega-3] and docosahexaenoic acid ["OHA"; cis-4, 7, 10, 13, 16, 19-docosahexaenoic acid; 22:6 omega-3] are required for fish growth and health and are often incorporated into commercial fish feeds via addition of fish oils.

It is estimated that aquaculture feed compositions currently use about 87% of the global supply of fish oil as a lipid source. Since annual fish oil production has not increased beyond 1.5 million tons per year, the rapidly growing aquaculture industry cannot continue to rely on finite stocks of marine pelagic fish as a supply of fish oil. Thus, there is great urgency to find and implement sustainable alternatives to fish oil that can keep pace with the growing global demand for fish products.

Many organizations recognize the limitations noted above with respect to fish oil availability and aquaculture sustainability. For example, in the United States, the National Oceanic and Atmospheric Administration is partnering with the Department of Agriculture in an Alternative Feeds Initiative to " . . . identify alternative dietary ingredients that will reduce the amount of fishmeal and fish oil contained in aquaculture feeds while maintaining the important human health benefits of farmed seafood".

U.S. Pat. No. 7,932,077 suggests recombinantly engineered *Yarrowia lipolytica* may be a useful addition to most animal feeds, including aquaculture feeds, as a means to provide necessary omega-3 and/or omega-6 PUFAs and based on its unique protein:lipid:carbohydrate composition, as well as unique complex carbohydrate profile (comprising an approximate 1:4:4.6 ratio of mannan:beta-glucans:chitin).

U.S. Pat. Appl. Pub. No. 2007/0226814 discloses fish food containing at least one biomass obtained from fermenting microorganisms wherein the biomass contains at least 20% DHA relative to the total fatty acid content. Preferred microorganisms used as sources for DHA are organisms belonging to the genus *Stramenopiles*.

If the growing aquaculture industry is to sustain its contribution to world fish supplies while producing aquaculture meat products that continue to provide health benefits for human consumption, then a reduction in the use wild fish is needed along with the adoption of more ecologically-sound management practices of the world fish supply

SUMMARY OF THE INVENTION

In one embodiment, the invention concerns a method of sustainably producing an aquaculture meat product by feeding a fish over its dietary cycles an aquaculture feed composition, said method comprising the step of formulating an aquaculture feed composition by replacing all or part of fish oil in the composition with a single microbial source of eicosapentaenoic acid ("EPA") and docosahexaenoic acid ("DHA").

In a preferred example, the microbial source comprising DHA and EPA is produced using a process based on the natural abilities of native microbes of *Schizochytrium* species.

In a second embodiment, the invention concerns a method of sustainably producing an aquaculture meat product by feeding a fish over its dietary cycles an aquaculture feed composition wherein the aquaculture feed composition comprises a total amount of EPA and DHA derived from said microbial source that is at least about 0.8% measured as a weight percent of the aquaculture feed composition.

In a third embodiment, the invention concerns a method of sustainably producing an aquaculture meat product by feeding a fish over its dietary cycles an aquaculture feed composition with a microbial oil source of EPA and DHA, wherein the microbial oil is provided in a form selected from the group consisting of: biomass, processed biomass, partially purified oil and purified oil, any of which is obtained from one microbe.

In a fourth embodiment, the invention concerns a feed additive composition for fish feed products, said additive composition comprises a single microbial source of eicosapentaenoic acid ("EPA") and docosahexaenoic acid ("DHA").

In a fifth embodiment, the invention concerns aquaculture feed with a microbial additive composition containing EPA and DHA, wherein the microbial additive is obtained from one single microbe.

In a sixth embodiment, the invention concerns a method of sustainably producing an aquaculture meat product by feeding a fish over its dietary cycles an aquaculture feed composition, said method comprising the step of formulating an aquaculture feed composition by replacing all or part of fish oil in the composition with a single microbial source of eicosapentaenoic acid ("EPA") and docosahexaenoic acid ("DHA"), wherein said microbe is a transgenic microbe genetically engineered for the production of polyunsaturated fatty acid containing microbial oil comprising EPA and DHA.

Preferably, the transgenic microbe is a microorganism of the order Thraustochytriales.

DETAILED DESCRIPTION

In this disclosure, a number of terms and abbreviations are used. The following definitions are provided:

"Polyunsaturated fatty acid(s)" is abbreviated as "PUFA(s)".
"Triacylglycerols" are abbreviated as "TAGs".
"Total fatty acids" are abbreviated as "TFAs".
"Fatty acid methyl esters" are abbreviated as "FAMEs".
"Dry cell weight" is abbreviated as "DCW".

As used herein the term "invention" or "present invention" is intended to refer to all aspects and embodiments of the invention as described in the claims and specification herein and should not be read so as to be limited to any particular embodiment or aspect.

The term "dietary cycles" of a fish refers to periods or stages of growth (i.e., growth stages) during which fish are fed a diet, or aquaculture feed, during aquaculture production. An example of dietary cycles for Atlantic Salmon is set forth in Table 1 below where there are six stages corresponding to the noted starting and ending weights. The dietary cycles in terms of number of stages, as well as starting and ending weights of fish for each stage, may vary for different types of fish and/or for different aquaculture practices.

TABLE 1

Exemplary Dietary Cycles or Stages of Fish Growth

| | Stage | | | | | |
|---|---|---|---|---|---|---|
| | 1 | 2 | 3 | 4 | 5 | 6 |
| Starting Weight (g) | 100 | 250 | 800 | 1500 | 2500 | 3500 |
| Ending Weight (g) | 250 | 800 | 1500 | 2500 | 3500 | 4500 |

The terms "aquaculture feed composition", "aquaculture feed formulation", "aquaculture feed" and "aquafeed" are used interchangeably herein. They refer to manufactured or artificial diets (i.e., formulated feeds) to supplement or to replace natural feeds in the aquaculture industry. These prepared foods are most commonly produced in flake, pellet or tablet form. Typically, an aquaculture feed composition refers to artificially compounded feeds that are useful for farmed finfish and crustaceans (i.e., both lower-value staple food fish species [e.g., freshwater finfish such as carp, tilapia and catfish] and higher-value cash crop species for luxury or niche markets [e.g., mainly marine and diadromous species such as shrimp, salmon, trout, yellowtail, seabass, seabream and grouper]). These formulated feeds are composed of ingredients in various proportions complementing each other to form a nutritionally complete diet for the aquacultured species. An aquaculture feed composition is used in the production of an "aquaculture product", wherein the product is a harvestable aquacultured species (e.g., finfish, crustaceans), which is often sold for human consumption. For example, salmon are intensively produced in aquaculture and thus are aquaculture products.

The term "aquaculture meat product" refers to food products intended for human consumption comprising at least a portion of meat from an aquaculture product as defined above. An aquaculture meat product may be, for example, a whole fish or a filet cut from a fish, each of which may be consumed as food.

"Eicosapentaenoic acid" ["EPA"] is the common name for eis-5, 8, 11,14, 17-eicosapentaenoic acid. This fatty acid is a 20:5 omega-3 fatty acid. The term EPA as used in the present disclosure will refer to the acid or derivatives of the acid (e.g., glycerides, esters, phospholipids, amides, lactones, salts or the like) unless specifically mentioned otherwise.

"Docosahexaenoic acid" ["DHA"] is the common name for eis-4, 7, 10, 13, 16, 19-docosahexaenoic acid. This fatty acid is a 22:6 omega-3 fatty acid. The term DHA as used in the present disclosure will refer to the acid or derivatives of the acid (e.g., glycerides, esters, phospholipids, amides, lactones, salts or the like) unless specifically mentioned otherwise.

As used herein the term "additive composition" refers to material derived from a microbial source which is provided in a form selected from the group consisting of: biomass, processed biomass, partially purified oil and purified oil, any of which is obtained from one single microbe.

As used herein the term "biomass" refers to microbial cellular material. Biomass may be produced naturally, or may be produced from the fermentation of a native host or a mutant strain or a recombinant production host. The biomass may be in the form of whole cells, whole cell-lysates, homogenized cells, partially hydrolyzed cellular material, and/or partially purified cellular material (e.g., microbially produced oil). The term "processed biomass" refers to biomass that has been subjected to additional processing such as drying, pasteurization, disruption, etc., each of which is discussed in greater detail below.

The term "lipids" refer to any fat-soluble (i.e., lipophilic), naturally occurring molecule. A general overview of lipids is provided in U.S. Pat. Appl. Pub. No. 2009-0093543-A1. The term "oil" refers to a lipid substance that is liquid at 25° C. and usually polyunsaturated.

The term "extracted oil" refers to oil that has been separated from cellular materials, such as the microorganism in which the oil was synthesized. Extracted oils are obtained through a wide variety of methods, the simplest of which involves physical means alone. For example, mechanical crushing using various press configurations (e.g., screw, expeller, piston, bead beaters, etc.) can separate oil from cellular materials. Alternatively, oil extraction can occur via treatment with various organic solvents (e.g., hexane), via enzymatic extraction, via osmotic shock, via ultrasonic extraction, via supercritical fluid extraction (e.g., $CO_2$ extraction), via saponification and via combinations of these methods. An extracted oil may be further purified or concentrated.

"Fish oil" refers to oil derived from the tissues of an oily fish. Examples of oily fish include, but are not limited to: menhaden, anchovy, herring, capelin, cod and the like. Fish oil is a typical component of feed used in aquaculture.

"Vegetable oil" refers to any edible oil obtained from a plant. Typically plant oil is extracted from seed or grain of a plant. The term "triacylglycerols" ["TAGs"] refers to neutral lipids composed of three fatty acyl residues esterified to a glycerol molecule.

TAGs can contain long chain PUFAs and saturated fatty acids, as well as shorter chain saturated and unsaturated fatty acids. "Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "total fatty acids" ["TFAs"] herein refers to the sum of all cellular fatty acids that can be derivatized to fatty acid methyl esters ["FAMEs"] by the base transesterification method (as known in the art) in a given sample, which may be biomass or oil, for example. Thus, total fatty acids include fatty acids from neutral lipid fractions (including diacylglycerols, monoacylglycerols and TAGs) and from polar lipid fractions (including, e.g., the phosphatidylcholine and phosphatidylethanolamine fractions) but not free fatty acids.

The term "total lipid content" of cells is a measure of TFAs as a percent of the dry cell weight ["DeW"]' although total lipid content can be approximated as a measure of FAMEs as a percent of the DeW ["FAMEs % DeW"]. Thus, total lipid content ["TFAs % DeW"] is equivalent to, e.g., milligrams of total fatty acids per 100 milligrams of DeW.

The concentration of a fatty acid in the total lipid is expressed herein as a weight percent of TFAs (% TFAs), e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its weight percent of the dry cell weight (% DCW). Thus, for example, eicosapentaenoic acid % DCW would be determined according to the following formula: (eicosapentaenoic acid % TFAs)*(TFAs % DCW)]/100. The content of a given fatty acid(s) in a cell as its weight percent of the dry cell weight (% DCW) can be approximated, however, as: (eicosapentaenoic acid % TFAs)*(FAMEs % DCW)]/100.

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "blended oil" refers to an oil that is obtained by admixing, or blending, the extracted oil described herein with any combination of, or individual, oil to obtain a desired composition. Thus, for example, types of oils from different microbes can be mixed together to obtain a desired PUFA composition. Alternatively, or additionally, the PUFA-containing oils disclosed herein can be blended with fish oil, vegetable oil or a mixture of both to obtain a desired composition.

The term "fatty acids" refers to long chain aliphatic acids (alkanoic acids) of varying chain lengths, from about C12 to C22, although both longer and shorter chain-length acids are known. The predominant chain lengths are between C16 and C22. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["00-6" or "n-6"] versus "omega-3 fatty acids" ["00-3" or "n-3"] are provided in U.S. Pat. No. 7,238,482, which is hereby incorporated herein by reference.

"Fish meal" refers to a protein source for aquaculture feed compositions. Fish meals are typically either produced from fishery wastes associated with the processing of fish for human consumption (e.g., salmon, tuna) or produced from specific fish (i.e., herring, menhaden) which are harvested solely for the purpose of producing fish meal.

Aquaculture is the practice of farming aquatic animals and plants. It involves cultivating an aquatic product (e.g., freshwater and saltwater animals) under controlled conditions. It involves growing and harvesting fish, shellfish, and aquatic plants in fresh, brackish or salt water.

Organisms grown in aquaculture may include fish and crustaceans. Crustaceans are, for example, lobsters, crabs, shrimp, prawns and crayfish. The farming of finfish is the most common form of aquaculture.

It involves raising fish commercially in tanks, ponds, or ocean enclosures, usually for food. A facility that releases juvenile fish into the wild for recreational fishing or to supplement a species' natural numbers is generally referred to as a fish hatchery. Particularly of interest are fish of the salmonid group, for example, cherry salmon (*Oncorhynchus masou*), Chinook salmon (*O. tshawytscha*), chum salmon (*O. keta*), coho salmon (*O. kisutch*), pink salmon (*O. gorbuscha*), sockeye salmon (*O. nerka*) and Atlantic salmon (*Salmo salar*). Other finfish of interest for aquaculture include, but are not limited to, various trout, as well as whitefish such as *tilapia* (including various species of *Oreochromis, Sarotherodon*, and *Tilapia*), sea bass, catfish (order Siluri-formes), bigeye tuna (*Thunnus obesus*), carp (family Cyprinidae) and cod (Gadus).

Aquaculture typically requires a prepared aquaculture feed composition to meet dietary requirements of the cultured animals. Dietary requirements of different aquaculture species vary, as do the dietary requirements of a single species during different stages of growth. Thus, tremendous research is invested towards optimizing each aquaculture feed composition for each stage of growth of a cultured organism.

Aquaculture feed compositions are composed of micro and macro components. In general, all components, which are used at levels of more than 1%, are considered as macro components. Feed ingredients used at levels of less than 1% are micro components. They are premixed to achieve a homogeneous distribution of the micro components in the complete feed. Both macro and micro ingredients are subdivided into components with nutritional functions and technical functions.

Components with technical functions improve the physical quality of the aquaculture feed composition or its appearance.

Macro components with nutritional functions provide aquatic animals with protein and energy required for growth and performance. With respect to fish, the aquaculture feed composition should ideally provide the fish with: 1) fats, which serve as a source of fatty acids for energy (especially for heart and skeletal muscles); and, 2) amino acids, which serve as building blocks of proteins. Fats also assist in vitamin absorption; for example, vitamins A, D, E and K are fat-soluble or can only be digested, absorbed, and transported in conjunction with fats. Carbohydrates, typically of plant origin (e.g., wheat, sunflower meal, corn gluten, soybean meal), are also often included in the feed compositions, although carbohydrates are not a superior energy source for fish over protein or fat.

Fats are typically provided via incorporation of fish meals (which contain a minor amount of fish oil) and fish oils into the aquaculture feed compositions. Extracted oils that may be used in aquaculture feed compositions include fish oils (e.g., from the oily fish menhaden, anchovy, herring, capelin and cod liver), and vegetable oil (e.g., from soybeans, rapeseeds, sunflower seeds and flax seeds). Typically, fish oil is the preferred oil, because it contains the long chain omega-3 polyunsaturated fatty acids ["PUFAs"], EPA and DHA; in contrast, vegetable oils do not provide a source of EPA and/or DHA. These PUFAs are needed for growth and health of most aquaculture products. A typical aquaculture feed composition will comprise from about 15-30% of oil (e.g., fish, vegetable, etc.), measured as a weight percent of the aquaculture feed composition.

The amount of EPA (as a percent of total fatty acids ["% TFAs"]) and DHA % TFAs provided in typical fish oils varies, as does the ratio of EPA to DHA. Typical values are summarized in Table 2, based on the work of Turchini, Torstensen and Ng (*Reviews in Aquaculture* 1:10-57 (2009)):

TABLE 2

Typical EPA and DHA Content in Various Fish Oils

| Fish Oil | EPA | DHA | EPA:DHA Ratio |
|---|---|---|---|
| Anchovy oil | 17% | 8.8% | 1.93:1 |
| Capelin oil | 4.6% | 3.0% | 1.53:1 |
| Menhaden oil | 11% | 9.7% | 1.21:1 |
| Herring oil | 8.4% | 4.9% | 1.71:1 |

The protein supplied in aquaculture feed compositions can be of plant or animal origin. For example, protein of animal origin can be from marine animals (e.g., fish meal, fish oil, fish protein, krill meal, mussel meal, shrimp peel, squid meal, squid oil, etc.) or land animals (e.g., blood meal, egg powder, liver meal, meat meal, meat and bone meal, silkworm, pupae meal, whey powder, etc.). Protein of plant origin can include soybean meal, corn gluten meal, wheat gluten, cottonseed meal, canola meal, sunflower meal, rice and the like.

The technical functions of macro components can be overlapping as, for example, wheat gluten may be used as a pelleting aid and for its protein content, which has a relatively high nutritional value. There can also be mentioned guar gum and wheat flour.

Micro components include feed additives such as vitamins, trace minerals, feed antibiotics and other biologicals. Minerals used at levels of less than 100 mg/kg (100 ppm) are considered as micro minerals or trace minerals.

Micro components with nutritional functions are all biologicals and trace minerals. They are involved in biological processes and are needed for good health and high performance. There can be mentioned vitamins such as vitamins A, E, K3, D3, B1, B3, B6, B12, C, biotin, folic acid, panthothenic acid, nicotinic acid, choline chloride, inositol and para-amino-benzoic acid. There can be mentioned minerals such as salts of calcium, cobalt, copper, iron, magnesium, phosphorus, potassium, selenium and zinc. Other components may include, but are not limited to, antioxidants, beta-glucans, bile salt, cholesterol, enzymes, monosodium glutamate, carotenoids, etc.

The technical functions of micro ingredients are mainly related to pelleting, detoxifying, mold prevention, antioxidation, etc.

In aquaculture, typically fish are fed in different dietary cycles as they grow. For example, Atlantic salmon may be fed in six different dietary cycles while growing from 100 grams to 4 kilograms as shown in Table 1 above. The weights of fish of different dietary cycles may vary depending on the type of fish and/or the aquaculture practice used.

In the second aspect, the aquaculture feed composition may comprise a total amount of EPA and DHA derived from a single microbial source that is at least about 0.8%, measured as weight percent of the aquaculture feed composition. This amount (i.e., 0.8%) is typically an appropriate minimal concentration that is suitable to support the growth of a variety of animals grown in aquaculture, and particularly is suitable for inclusion in the diets of salmonid fish.

As previously discussed, the highest EPA:DHA ratio in fish oil (i.e., anchovy oil) was 1.93:1 (Turchini, Torstensen and Ng, supra) and the lowest EPA:DHA ratio in fish oil was 1.21:1. Thus, it is believed that no commercially available aquaculture feed composition has been produced having an EPA:DHA ratio greater than 1.93:1 or lower than 1.21:1.

To achieve an EPA:DHA ratio greater than 2:1 or lower than 1.2:1, as described herein, an alternate source of EPA and DHA is required.

In one example, the aquaculture feed compositions of the present invention comprise one source of DHA and EPA, wherein the ratio of EPA:DHA is greater than 2:1 based on the individual concentrations of EPA and DHA, each measured as a weight percent of total fatty acids in the microbial source or in the aquaculture feed composition.

In another example, the aquaculture feed compositions of the present invention comprise one source of DHA and EPA, wherein the ratio of EPA:DHA is lower than 1:1, preferably between 0.2:1 and 1:1 based on the individual concentrations of EPA and DHA, each measured as a weight percent of total fatty acids in the microbial source or in the aquaculture feed composition.

Most processes to make an aquaculture feed composition of the invention will begin with a microbial fermentation, wherein a particular microorganism is cultured under conditions that permit growth and production of microbial oils comprising EPA and DHA. At an appropriate time, the microbial cells are harvested from the fermentation vessel. This microbial biomass may be mechanically processed using various means, such as dewatering, drying, mechanical disruption, pelletization, etc. Then, the biomass (or extracted oil therefrom) is used as an ingredient in an aquaculture feed (preferably as a substitute for at least a portion of the fish oil used in standard aquaculture feed compositions). The aquaculture feed is then fed to aquatic animals over a portion of their lifetime, such that EPA and DHA from the aquaculture feed accumulate in the aquatic animals. Upon harvesting, the resulting aquaculture meat product will thereby comprise a ratio of EPA/DHA that is equal to or greater than 2:1 or equal or lower than 1:1. Each of these aspects will be discussed in further detail below.

Microbial oils comprising EPA and DHA according to the present invention may be provided in a variety of forms for use in the aquaculture feed compositions herein, wherein the oil is typically contained within microbial biomass or processed biomass, or the oil is partially purified or purified oil. In most cases, it will be most cost effective to incorporate microbial biomass or processed biomass into the aquaculture feed composition, as opposed to the microbial oil (in partial or purified form); however, these economics should not be considered as a limitation herein.

The microorganism according to the present invention is an algae, fungi or yeast. Preferred microbes are Thraustochytrids which are microorganisms of the order Thraustochytriales. Thraustochytrids include members of the genus *Schizochytrium* and *Thraustochytrium* and have been recognized as an alternative source of omega-3 fatty acids, including DHA and EPA. See U.S. Pat. No. 5,130,242.

In a preferred embodiment the microorganism is a mutant strain of the species *Schizochytrium*. *Schizochytrium* strains are natural sources of PUFAs such as DHA and can be optimized by mutagenesis to be used as microbial source according to the present invention.

DHA and EPA producing *Schizochytrium* strains can be obtained by consecutive mutagenesis followed by suitable selection of mutant strains which demonstrate superior EPA and DHA production and a specific EPA:DHA ratio. Starting wild type strains include those on deposit with the various culture collections throughout the world, e.g. the ATCC and the Centraalbureau voor Schimmelcultures (CBS). Typically it is necessary to perform two or more consecutive rounds of mutagenesis to obtain desirable mutant strains.

Any chemical or nonchemical (e.g. ultraviolet (UV) radiation) agent capable of inducing genetic change to the yeast cell can be used as the mutagen. These agents can be used alone or in combination with one another, and the chemical agents can be used neat or with a solvent.

For example, a strain can be mutated and selected such that it produces EPA and DHA in amounts to be commercially viable and with a EPA:DHA ratio equal to or greater than 2:1 and may with a ratio of at least about 2.2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 or higher. Alternatively the strain can be mutated and selected such that it produces EPA and DHA in amounts to be commercially viable and with a EPA:DHA ratio equal to or lower than 1:1 and may with a ratio of about 0.9:1, 0.8:1, 0.7:1, 0.6:1, 0.5:1, 0.4:1, 0.3:1, 0:2:1 or lower.

Alternately, the microbial source according the invention can be produced by microbes genetically transformed for the production of the PUFAs. Optionally the microorganism may be engineered for production of DHA and EPA by expressing appropriate heterologous genes encoding for example desaturases and elongases of either the delta-6 desaturase/delta-6 elongase pathway or the delta-9 elongase/delta-8 desaturase pathway in the host organism.

Heterologous genes in expression cassettes are typically integrated into the host cell genome. The particular gene(s) included within a particular expression cassette depend on the host organism, its PUFA profile and/or desaturase/elongase profile, the availability of substrate and the desired end product(s). A PUFA polyketide synthase ["PKS"] system that produces EPA, such as that found in e.g., *Shewanella putrefaciens* (U.S. Pat. No. 6,140,486), *Shewanella olleyana* (U.S. Pat. No. 7,217,856), *Shewanella japonica* (U.S. Pat. No. 7,217,856) and *Vibrio marinus* (U.S. Pat. No. 6,140,486), could also be introduced into a suitable DHA producing microbe to enable EPA and DHA production. Host organisms with other PKS systems that natively produce DHA could also be engineered to enable production of a suitable combination of the PUFAs to yield an EPA:DHA ratio of greater than 2:1 or lower than 1:1. One skilled in the art is familiar with the considerations and techniques necessary to introduce one or more expression cassettes encoding appropriate enzymes for EPA and DHA biosynthesis into a microbial host organism of choice, and numerous teachings are provided in the literature to one of skill. Microbial oils comprising EPA and DHA from these genetically engineered organisms may also be suitable for use in the aquaculture feed compositions herein, wherein the oil may be contained within the microbial biomass or processed biomass, or the oil may be partially purified or purified oil.

Typical species of microorganisms useful for the present invention are deposited under ATCC Accession No. PTA-10208, PTA-10209, PTA-10210, or PTA-10211, PTA-10212, PTA-10213, PTA-10214, PTA-10215.

In some embodiments, the invention is directed to an isolated microorganism having the characteristics of the species deposited under ATCC Accession No. PTA-10212 or a strain derived therefrom. The characteristics of the species deposited under ATCC Accession No. PTA-10212 can include its growth and phenotypic properties (examples of phenotypic properties include morphological and reproductive properties), its physical and chemical properties (such as dry weights and lipid profiles), its gene sequences, and combinations thereof, in which the characteristics distinguish the species over previously identified species. In some embodiments, the invention is directed to an isolated microorganism having the characteristics of the species deposited under ATCC Accession No. PTA-10212, wherein the characteristics include an 18s rRNA comprising the polynucleotide sequence of SEQ ID NO1 or a polynucleotide sequence having at least 94%, 95%, 96%, 97%, 98%, or 99% identity to SEQ ID NO1, the morphological and reproductive properties of the species deposited under ATCC Accession No. PTA-10212, and the fatty acid profiles of the species deposited under ATCC Accession No. PTA-10212.

In further embodiments, the mutant strain is a strain deposited under ATCC Accession No. PTA-10213, PTA-10214, or PTA-10215. The microorganisms associated with ATCC Accession Nos. PTA-10213, PTA-10214, and PTA-10215 were deposited under the Budapest Treaty on Jul. 14, 2009 at the American Type Culture Collection, Patent Depository, 10801 University Boulevard, Manassas, VA 201 10-2209.

In some embodiments, the invention is directed to an isolated microorganism of the species deposited under ATCC Accession No. PTA-10208. The isolated microorganism associated with ATCC Accession No. PTA-10208 is also known herein as *Schizochytrium* sp. ATCC PTA-10208. The microorganism associated with ATCC Accession No. PTA-10208 was deposited under the Budapest Treaty on Jul. 14, 2009 at the American Type Culture Collection, Patent Depository, 10801 University Boulevard, Manassas, VA 20110-2209.

In some embodiments, the invention is directed to a mutant strain of the microorganism deposited under ATCC Accession No. PTA-10208. In further embodiments, the mutant strain is a strain deposited under ATCC Accession No. PTA-10209, PTA-10210, or PTA-1021 1. The microorganisms associated with ATCC Accession Nos. PTA-10209, PTA-10210, and PTA-1021 1 were deposited under the Budapest Treaty on Sep. 25, 2009 at the American Type Culture Collection, Patent Depository, 10801 University Boulevard, Manassas, VA 20110-2209.

A microbe according to the present invention may be cultured and grown in a fermentation medium under conditions whereby the PUFAs are produced by the microorganism. Typically, the microorganism is fed with a carbon and nitrogen source, along with a number of additional chemicals or substances that allow growth of the microorganism and/or production of EPA and DHA. The fermentation conditions will depend on the microorganism used and may be optimized for a high content of the desired PUFA(s) in the resulting biomass.

In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest.

When the desired amount of EPA and DHA has been produced by the microorganism(s), the fermentation medium may be treated to obtain microbial biomass comprising the PUFA(s). For example, the fermentation medium may be filtered or otherwise treated to remove at least part of the aqueous component. The fermentation medium and/or the microbial biomass may be further processed, for example the microbial biomass may be pasteurized or treated via other means to reduce the activity of endogenous microbial enzymes that can harm the microbial oil and/or PUFAs. The microbial biomass may be subjected to drying (e.g., to a desired water content) or a means of mechanical disruption (e.g., via physical means such as bead beaters, screw extrusion, etc. to provide greater accessibility to the cell contents), or a combination of these. The microbial biomass may be granulated or pelletized for ease of handling. Thus, microbial biomass obtained from any of the means described above may be used as a source of microbial oil comprising EPA and DHA. This source of microbial oil may then be used as an ingredient in the aquaculture feed compositions.

In the first examples of the present invention, aquaculture meat products comprising EPA and DHA in a ratio that is equal to or greater than 2:1, based on the concentration of each of EPA and DHA in the aquaculture meat product, are sustainably produced. The ratio of concentration of each of EPA to DHA may be equal to or greater than 2:1, 2.1:1, 2.2:1, 2.3:1, 2.4:1, 2.5:1, 2.6:1, 2.7:1, 2.8:1, 2.9:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 or higher.

In the second examples of the present invention, aquaculture meat products comprising EPA and DHA in a ratio that is equal to or lower than 1:1, based on the concentration of each of EPA and DHA in the aquaculture meat product, are sustainably produced. The ratio of concentration of each of EPA to DHA may be equal to or lower than 1:1, 0.9:1, 0.8:1, 0.7:1, 0.6:1, 0.5:1, 0.4:1, 0.3:1, 0:2:1 or lower.

A preferred example of a microbial oil according to the invention is an oil from *Schizochytrium* containing
 at least 40% w/w DHA & EPA, preferably about 50% w/w DHA & EPA,
 an EPA:DHA ratio of about 0, 2:1 to 1:1, preferably 0, 4:1 to 0, 8:1, and
 at least one antioxidant which is added to provide stability.

Microbial oil as described and obtained from any of the means described above may be used as a single source of EPA and DHA for use in aquaculture feed compositions that are fed to aquaculture animals to produce aquaculture meat products having an EPA:DHA ratio equal to or greater than 2:1 or equal to or less than 1:1.

Aquaculture meat products obtained using the method of the invention may further comprise a total amount of EPA and DHA that is at least about 0.5% as a weight percent of the aquaculture meat product. This amount is an amount that typically is present in aquaculture meat products.

A total amount of EPA and DHA that is at least about 0.5% as weight percent of an aquaculture meat product may be obtained by feeding aquaculture animals with an aquaculture feed composition having a sum of EPA plus DHA that is typically at least about 1.6% of the aquaculture feed composition by weight.

Based on the disclosure herein, it will be clear that renewable alternatives to fish oil can be utilized, as a means to sustainably produce aquaculture feed compositions over the dietary cycles of a fish.

Having generally described this invention, a further understanding can be obtained by reference to the examples provided herein. These examples are for purposes of illustration only and are not intended to be limiting.

EXAMPLE 1 GROWTH CHARACTERISTICS OF THE ISOLATED MICROORGANISM DEPOSITED UNDER ATCC ACCESSION NO. PTA-10212

The isolated microorganism deposited under ATCC Accession No. PTA-10212 was examined for growth characteristics in individual fermentation runs, as described below. Typical media and cultivation conditions are shown in Table 3.

TABLE 3

PTA-10212 Vessel Media

| Ingredient | | concentration | ranges |
|---|---|---|---|
| $Na_2SO_4$ | g/L | 31.0 | 0-50, 15-45, or 25-35 |
| NaCl | g/L | 0.625 | 0-25, 0.1-10, or 0.5-5 |
| KCl | g/L | 1.0 | 0-5, 0.25-3, or 0.5-2 |
| $MgSO_4*7H_2O$ | g/L | 5.0 | 0-10, 2-8, or 3-6 |
| $(NH_4)_2SO_4$ | g/L | 0.44 | 0-10, 0.25-5, or 0.05-3 |
| $MSG*1H2O$ | g/L | 6.0 | 0-10, 4-8, 01-5-7 |
| $CaCl_2$ | g/L | 0.29 | 0.1-5, 0.15-3, or 0.2-1 |
| T 154 (yeast extract) | g/L | 6.0 | 0-20, 0.1-10, or 1-7 |
| $KH_2PO_4$ | g/L | 0.8 | 0.1-10, 0.5-5, or 0.6-1.8 |
| Post autoclave (Metals) | | | |
| Citric acid | mg/L | 3.5 | 0.1-5000, 10-3000, or 3-2500 |
| $FeSO_4*7H_2O$ | mg/L | 10.30 | 0.1-100, 1-50, or 5-25 |
| $MnCl_2*4H_2O$ | mg/L | 3.10 | 0.1-100, 1-50, or 2-25 |
| $ZnSO_4*7H_2O$ | mg/L | 3.10 | 0.01-100, 1-50, or 2-25 |
| $CoCl_2*6H_2O$ | mg/L | 0.04 | 0-1, 0.001-0.1, or 0.01-0.1 |
| $Na_2MoO_4*2H_2O$ | mg/L | 0.04 | 0.001-1, 0.005-0.5, or 0.01-0.1 |
| $CuSO_4*5H_2O$ | mg/L | 2.07 | 0.1-100, 0.5-50, or 1-25 |
| $NiSO_4*6H_2O$ | mg/L | 2.07 | 0.1-100, 0.5-50, or 1-25 |
| Post autoclave (Vitamins) | | | |
| Thiamine | mg/L | 9.75 | 0.1-100, 1-50, or 5-25 |
| Vitamin B 12 | mg/L | 0.16 | 0.01-100, 0.05-5, or 0.1-1 |
| Ca[1/2]-pantothenate | mg/L | 2.06 | 0.1-100, 0.1-50, or 1-10 |
| Biotin | mg/L | 3.21 | 0.1-100, 0.1-50, or 1-10 |
| Post autoclave (Carbon) | | | |
| Glycerol | g/L | 30.0 | 5-150, 10-100, or 20-50 |

TABLE 3-continued

PTA-10212 Vessel Media

| Ingredient | | | concentration ranges |
|---|---|---|---|
| Nitrogen Feed: | | | |
| MSG*1H$_2$O | g/L | 17 | 0-150, 10-100, or 15-50 |

Typical cultivation conditions would include the following:
- pH 6.5-9.5, about 6.5-about 8.0, or about 6.8-about 7.8;
- temperature: 15-30 degrees Celsius, about 18-about 28 degrees Celsius, or about 21 to about 23 degrees Celsius;
- dissolved oxygen: 0.1-about 100% saturation, about 5-about 50% saturation, or about 10-about 30% saturation; and/or
- glycerol controlled @: 5-about 50 g/L, about 10-about 40 g/L, or about 15-about 35 g/L.

In carbon (glycerol) and nitrogen-fed cultures with 1000 ppm Cl at 22.5° C. with 20% dissolved oxygen at pH 7.3, PTA-10212 produced a dry cell weight of 26.2 g/L after 138 hours of culture in a 10 L fermentor volume. The lipid yield was 7.9 g/L; the omega-3 yield was 5.3 g/L; the EPA yield was 3.3 g/L and the DHA yield was 1.8 g/L. The fatty acid content was 30.3% by weight; the EPA content was 41.4% of fatty acid methyl esters (FAME); and the DHA content was 26.2% of FAME. The lipid productivity was 1.38 g/L/day, and the omega-3 productivity was 0.92 g/L/day under these conditions, with 0.57 g/L/day EPA productivity and 0.31 g/L/day DHA productivity.

In carbon (glycerol) and nitrogen-fed cultures with 1000 ppm Cl at 22.5° C. with 20% dissolved oxygen at pH 7.3, PTA-10212 produced a dry cell weight of 38.4 g/L after 189 hours of culture in a 10 L fermentor volume. The lipid yield was 18 g/L; the omega-3 yield was 12 g/L; the EPA yield was 5 g/L and the DHA yield was 6.8 g/L. The fatty acid content was 45% by weight; the EPA content was 27.8% of FAME; and the DHA content was 37.9% of FAME. The lipid productivity was 2.3 g/L/day, and the omega-3 productivity was 1.5 g/L/day under these conditions, with 0.63 g/L/day EPA productivity and 0.86 g/L/day DHA productivity.

In carbon (glycerol) and nitrogen-fed cultures with 1000 ppm Cl at 22.5° C. with 20% dissolved oxygen at pH 6.8-7.7, PTA-10212 produced a dry cell weight of 13 g/L after 189 hours of culture in a 10 L fermentor volume. The lipid yield was 5.6 g/L; the omega-3 yield was 3.5 g/L; the EPA yield was 1.55 g/L and the DHA yield was 1.9 g/L. The fatty acid content was 38% by weight; the EPA content was 29.5% of FAME; and the DHA content was 36% of FAME. The lipid productivity was 0.67 g/L/day, and the omega-3 productivity was 0.4 g/L/day under these conditions, with 0.20 g/L/day EPA productivity and 0.24 g/L/day DHA productivity.

In carbon (glycerol) and nitrogen-fed cultures with 1000 ppm C at 22.5-28.5° C. with 20% dissolved oxygen at pH 6.6-7.2, PTA-10212 produced a dry cell weight of 36.7 g/L-48.7 g/L after 191 hours of culture in a 10 L fermentor volume. The lipid yield was 15.2 g/L-25.3 g/L; the omega-3 yield was 9.3 g/L-13.8 g/L; the EPA yield was 2.5 g/L-3.3 g/L and the DHA yield was 5.8 g/L-1 1 g/L. The fatty acid content was 42.4%-53% by weight; the EPA content was 9.8%-22% of FAME; and the DHA content was 38.1%-43.6% of FAME. The lipid productivity was 1.9 g/L/day-3.2 g/L/day, and the omega-3 productivity was 1.2 g/L/day-1.7 g/L/day under these conditions, with 0.31 g/L/day-0.41 g/L/day EPA productivity and 0.72 g/L/day-1.4 g/L/day DHA productivity.

EXAMPLE 2 APPARENT DIGESTIBILITY OF DHA AND EPA AS MICROBIAL BIOMASS IN ATLANTIC SALMON

Atlantic salmon of initial body weight ca 200 g were randomly distributed into 1.5 m tanks with 50 fish per tank. The water temperature was in the range of 10° C. Fish were adapted to the control diet for 2 weeks before starting feeding the experimental diets.

A 3-mm diet was produced by extrusion at Nofima in Bergen according to the formulation described in table 4. Only rapeseed oil was added to the diet and the basal levels of DHA and EPA in the control diet comes from the fish meal which has been included in the diet at a level of ca. 23%. NO fish oil was added to the diet.

As microbial source of DHA and EPA the biomass of a species of *Schizochytrium* sp. ATCC PTA-10208 also known as OvegaGold™ has been used. The biomass inclusions were 0, 0.9, 3.5 and 6.2% of the diet which corresponds to DHA levels of 0, 0.5, 1.0, 1.5%.

Fish were fed for at least 4 weeks and each dietary treatment was performed in triplicates. After 4 weeks of experimental feeding, feces were collected by stripping each fish from each individual tank. Muscle sample was taken out from five fish per tank.

Apparent digestibility coefficients were determined for the omega-3 fatty acids and for the nutrients such as dry matter, lipids and protein.

Statistical analysis was performed using Statbox Pro (one-way ANOVA).

TABLE 4

| Diet formulation | | | | |
|---|---|---|---|---|
| Major diet ingredients (%) | Ctrl | OvegaGold providing 0.5% DHA | OvegaGold providing 1.0% DHA | OvegaGold providing 1.5% DHA |
| Fish meal | 23 | 22 | 22.4 | 22 |
| Soy protein conc. | 17 | 17 | 17 | 17 |
| Rapeseed oil | 22 | 21 | 20 | 19 |
| Wheat meal | 11.4 | 10.9 | 8.7 | 7.4 |
| Corn gluten | 5 | 5 | 5 | 5 |
| Wheat gluten | 13 | 13 | 13 | 13 |
| Pea protein concentrate | 2 | 2 | 2 | 2 |
| OvegaGold | 0 | 2.5 | 5.2 | 8.0 |

Results of in-feed recovery of DHA and EPA are presented in Table 5. Results show a very good recovery of DHA and EPA after feed processing by extrusion and a clear dose response.

TABLE 5

| In feed recovery | | | | |
|---|---|---|---|---|
| | Recovery (mg/g) | | | |
| Treatments | EPA | DHA | EPA + DHA | Total Ω-3 |
| Control | 2.21 | 4.32 | 6.53 | 25.81 |
| OvegaGold providing 0.5% DHA | 4.31 | 9.61 | 13.92 | 34.26 |
| From supplementation | 2.1 | 5.3 | 6.4 | |

TABLE 5-continued

| | In feed recovery | | | |
|---|---|---|---|---|
| | Recovery (mg/g) | | | |
| Treatments | EPA | DHA | EPA + DHA | Total Ω-3 |
| OvegaGold providing 1.0% DHA | 5.57 | 12.80 | 18.37 | 37.38 |
| From supplementation | 3.4 | 8.5 | 11.9 | |
| OvegaGold providing 1.5% DHA | 7.52 | 17.64 | 25.16 | 43.38 |
| From supplementation | 5.3 | 13.3 | 18.6 | |

Figure 1:
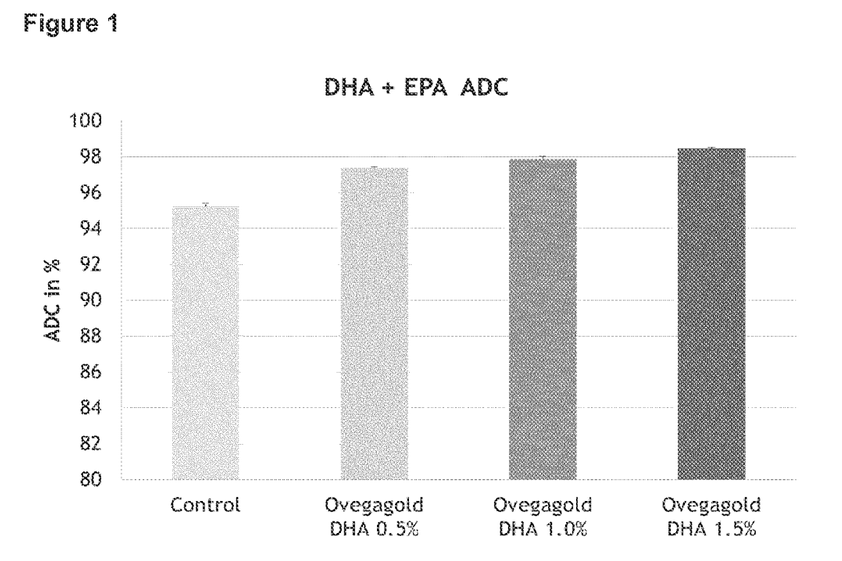
Figure 2:
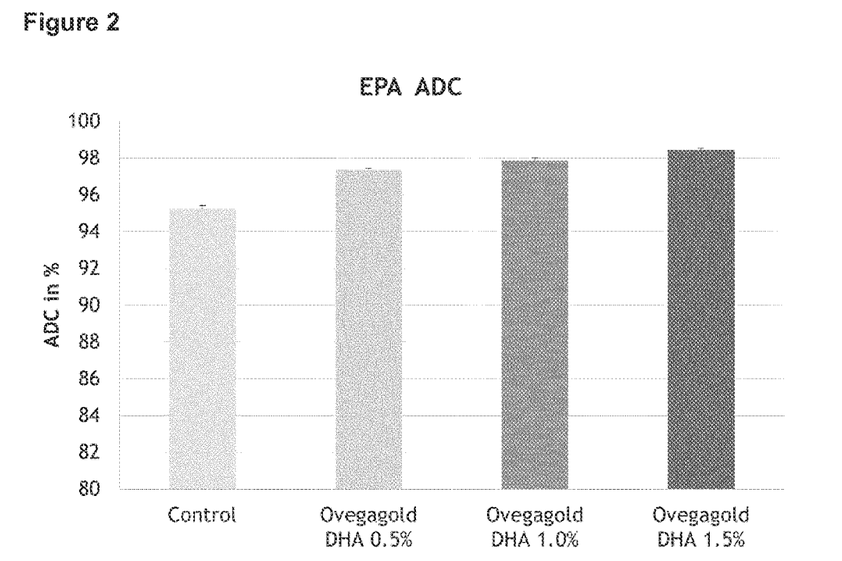
Figure 3:
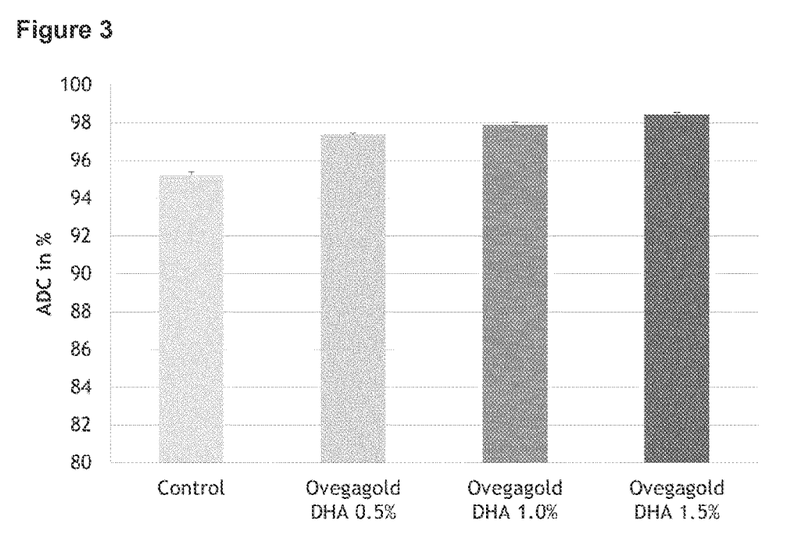

Apparent digestibility coefficient was determined for DHA, EPA, DHA+EPA and omega-3 fatty acids. FIGS. 1, 2 and 3 present the digestibly of DHA+EPA, EPA and DHA, respectively. Results show that EPA and DHA provided via an algal source are highly digestible.

FIG. 1: Apparent digestibility of DHA in the diet supplemented with graded amounts of OvegaGold. Results of statistical analysis are presented in Table 6.

FIG. 2: Apparent digestibility of EPA in the diet supplemented with graded amounts of OvegaGold. Results of statistical analysis are presented in Table 6.

FIG. 3: Apparent digestibility of DHA in the diet supplemented with graded amounts of OvegaGold. Results of statistical analysis are presented in Table 6.

Figure 4:
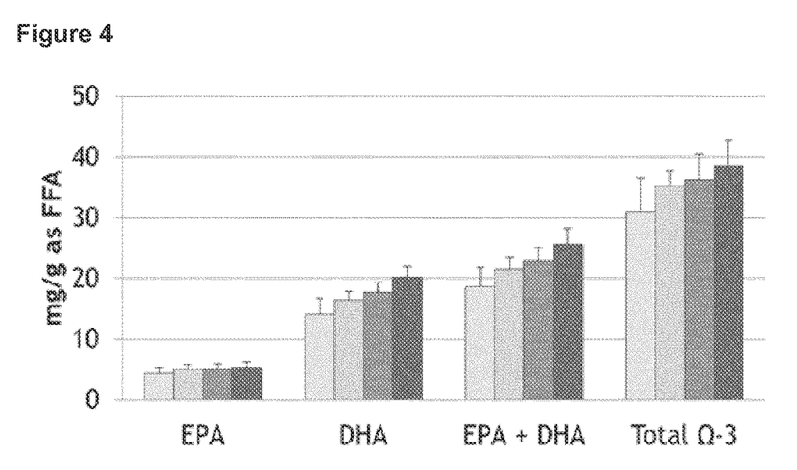

FIG. 4: Muscle deposition of omega-3 fatty acids following ca 4 weeks of feeding the experimental diets. Muscle content confirms the high bioavailability of omega-3 fatty acids from a microalgal source.

TABLE 6

| | Apparent digestibility coefficients as mean ± Sd | | | | | | | |
|---|---|---|---|---|---|---|---|---|
| | ADC (%) | | | | | | | |
| Treatment | EPA | ±SD | DHA | ±SD | EPA + DHA | ±SD | Total Ω 3 | ±SD |
| Control | 97.35 | 0.05 | 94.18 | 0.23 | 95.25 | 0.17 | 98.36 | 0.07 |
| OvegaGold 0.5% DHA | 98.50 | 0.06 | 96.96 | 0.06 | 97.40 | 0.06 | 98.65 | 0.02 |
| OvegaGold 1.0% DHA | 98.72 | 0.16 | 97.52 | 0.14 | 97.88 | 0.14 | 98.69 | 0.11 |
| OvegaGold 1.5% DHA | 99.05 | 0.05 | 98.19 | 0.14 | 98.44 | 0.11 | 98.90 | 0.08 |

As a conclusion, DHA and EPA are highly bioavailable when provided as a microalgal biomass supplemented to a salmon diet.

The invention claimed is:

1. A method of sustainably producing an aquaculture meat product which comprises feeding an aquaculture feed composition to a fish over dietary cycles of the fish, wherein
all or part of fish oil in the aquaculture feed composition is replaced with a single microbial source of eicosapentaenoic acid (EPA) and docosahexaenoic acid (DHA), and wherein
the microbial source is microbial oil which is provided in a form which is obtained from the single microbial source and is selected from the group consisting of biomass, processed biomass, partially purified oil and purified oil, and wherein
the aquaculture feed composition has a ratio of concentration of the EPA to concentration of the DHA which is at least 2:1, based on individual concentrations of EPA and DHA in the aquaculture meat product.

2. The method of claim 1, wherein the aquaculture feed composition comprises a total amount of EPA and DHA that is at least about 0.8%, measured as a weight percent of the aquaculture feed composition.

3. The method of claim 1, wherein the microbial source is derived from a microorganism selected from the group consisting of algae, fungi and yeast.

4. The method of claim 3, wherein the microorganism is a member of the genus *Schizochytrium* or *Thraustochytrium*.

5. The method of claim 4, wherein the microorganism has the characteristics of the species deposited under ATCC Accession No. PTA-10208 or PTA-10209 or PTA-10210 or PTA-10211 or PTA-10212 or PTA-10213 or PTA-10214 or PTA-10215.

6. The method of claim 3, wherein the microorganism is a mutant strain.

7. The method of claim 3, wherein the microorganism is a transgenic microbe genetically engineered for the production of polyunsaturated fatty acid containing microbial oil comprising EPA and DHA.

8. A feed additive composition for aquaculture feed comprising:
eicosapentaenoic acid (EPA) and docosahexaenoic acid (DHA) derived from a single microbial source, wherein
the feed additive composition is a purified microbial oil form comprising at least 40% w/w of the EPA and the DHA; and wherein
the purified microbial oil has a ratio of concentration of the EPA to concentration of the DHA of about 0.2:1 to about 1:1.

9. The feed additive composition of claim 8, wherein the microbial source is derived from a microorganism selected from the group consisting of algae, fungi and yeast.

10. The feed additive composition of claim 9, wherein the microorganism is a member of the genus *Schizochytrium* or *Thraustochytrium*.

11. The feed additive composition of claim 10, wherein the microorganism has the characteristics of the species deposited under ATCC Accession No. PTA-10208 or PTA-10209 or PTA-10210 or PTA-10211 or PTA-10212 or PTA-10213 or PTA-10214 or PTA-10215.

12. The feed additive composition of claim 8, wherein the feed additive composition is a purified microbial oil form comprising about 50% w/w of the DHA and the EPA.

13. An aquaculture feed comprising:
a single microbial source of eicosapentaenoic acid (EPA) and docosahexaenoic acid (DHA), wherein
the microbial source is a microbial oil comprising at least 40% w/w of the EPA and the DHA which is provided in a form selected from the group consisting of biomass, processed biomass, partially purified oil and purified oil, any of which is obtained from the microbial source, and wherein the microbial oil has a ratio of concentration of the EPA to concentration of the DHA of about 0.2:1 to about 1:1.

14. The aquaculture feed of claim 13 comprising a total amount of EPA and DHA that is at least about 0.08%, measured as a weight percent of the feed.

15. The aquaculture feed of claim 13, wherein the microbial source is derived from a microorganism selected from the group consisting of algae, fungi and yeast.

16. The aquaculture feed of claim 15, wherein the microorganism is a member of the genus *Schizochytrium* or *Thraustochytrium*.

17. The aquaculture feed of claim 16, wherein the microorganism has the characteristics of the species deposited under ATCC Accession No. PTA-10208 or PTA-10209 or PTA-10210 or PTA-10211 or PTA-10212 or PTA-10213 or PTA-10214 or PTA-10215.

* * * * *